United States Patent [19]

Bigliardi et al.

[11] Patent Number: 5,020,628
[45] Date of Patent: Jun. 4, 1991

[54] VEHICULAR IGNITION INTERLOCK SYSTEM

[75] Inventors: Achille M. Bigliardi, Woodside; Terry R. Jablonski, San Jose, both of Calif.

[73] Assignee: Sencion Corporation, Woodside, Calif.

[21] Appl. No.: 446,390

[22] Filed: Dec. 5, 1989

[51] Int. Cl.$^5$ .............................................. B60K 28/06
[52] U.S. Cl. ................................... 180/272; 128/719; 340/576; 422/84; 73/23.2
[58] Field of Search ................. 180/272; 340/506, 507, 340/521, 562, 576, 522, 527; 73/23.2, 23.1; 128/719; 422/84, 85

[56] References Cited

U.S. PATENT DOCUMENTS

| | | | |
|---|---|---|---|
| 3,824,538 | 7/1974 | Slemp | 340/576 |
| 4,300,385 | 11/1981 | Albarda | 73/23.1 |
| 4,697,666 | 10/1987 | Collier et al. | 180/272 |
| 4,716,413 | 12/1987 | Haile | 180/272 |
| 4,723,625 | 2/1988 | Komlos | 180/272 |
| 4,809,810 | 3/1989 | Elfman | 180/272 |

Primary Examiner—Richard A. Bertsch
Attorney, Agent, or Firm—Fliesler, Dubb, Meyer & Lovejoy

[57] ABSTRACT

A vehicular ignition interlock system having a flow rate integrator and a servograph. The integrator is provided to insure that only "deep lung air" is analyzed for alcohol. A pressure transducer is employed in the integrator such that the output of the transducer is proportional to the air flow rate. As the rate of flow of a breath sample varies, a corresponding change in the required duration of the breath sample is made to insure that a deep lung air sample is being analyzed. The servograph comprises a plurality of colored lights and a tone generator which are controlled by a computer to direct the operator to adjust the rate of flow of his or her breath sample in accordance with the visual indication provided by the lights. Thus the servograph and the flow rate integrator insure that only a human subject will be capable of providing the air sample to be analyzed. A gas sensor and flow sensor are mounted in a replaceable module to facilitate field repair, replacement and calibration.

45 Claims, 6 Drawing Sheets

VEHICULAR IGNITION INTERLOCK SYSTEM

BACKGROUND OF THE INVENTION

1. Field of the Invention

The present invention relates to alcohol breath analyzers in general and in particular to a vehicular ignition interlock system comprising an alcohol breath analyzer for enabling the operation of a motor vehicle when the operator thereof has a blood alcohol concentration (BAC) below predetermined threshold level.

2. Description of the Prior Art

A vehicular ignition interlock system for testing the blood alcohol concentration (BAC) of a driver is used for preventing the operation of a motor vehicle by the driver until the driver passes a test demonstrating that his or her BAC is below a predetermined threshold level.

A number of vehicular ignition interlock systems which test for BAC have been proposed. In general, they have required that a person provide a continuous, uninterrupted flow of breath at or above a certain pressure for a predetermined period of time. The pressure and time limitations are intended to insure that the test will comprise a deep lung or alveolar air sample as distinguished from an air sample from the upper portions of the respiratory tract. A deep lung sample which produces gas present in the alveoli of the lungs which has an alcohol content directly proportional to the BAC in the blood stream is required to obtain an accurate measure of BAC. Air samples from the upper portions of the respiratory tract, as is typically provided by short multiple exhalations, are insufficient. Such a system, for example, is disclosed in Collier et al, U.S. Pat. No. 4,093,945.

A disadvantage of the prior known systems described above is that the requirement that a person maintain a continuous, uninterrupted flow of breath at or above a certain pressure for a predetermined period of time in order to pass the test may be difficult for some people to achieve if the required pressure is too high and/or the predetermined period is too long.

Another disadvantage of the prior known systems as described above is that they can be defeated by using a bogus air source such as a pre-filled balloon, air pump or the like for providing the air sample.

Various means have been employed to prevent the use of a bogus air source. For example, in Collier et al, U.S. Pat. No. 4,738,333, there is disclosed a system for confirming the identity of the operator which requires the operator to perform a pre-learned identity-confirming physical act. The act may comprise, for example, any one of a number of breathing sequences, difficult to duplicate in a short time, comprising periods of blowing and non-blowing. In Elfman et al, U.S. Pat. No. 4,678,057, there is disclosed a system which requires the acquiring and storing of a reference breath signature which is compared against a breath sample which is taken during testing.

While possibly necessary for preventing a sober person from taking the test for an inebriated person, the above-described apparatus and methods are seen as being too complex, expensive and difficult to use if what is desired is to simply prevent an inebriated person from using a pre-filled balloon, air pump or the like as a source of an air sample in order to defeat the system.

SUMMARY OF THE INVENTION

In view of the foregoing, principal objects of the present invention are a novel and improved method and apparatus comprising an alcohol breath analyzer for preventing the operation of a motor vehicle or other manually operated machine unless and until the operator thereof passes an alcohol breath test.

In accordance with the above objects, there is provided a flow rate integrator and a servograph which operate in conjunction to insure that a deep lung sample is acquired from the operator and that a human and not a bogus air source, such as a pre-filled balloon, air pump or the like, is providing the sample.

In the flow rate integrator there is provided a tubular member, the lower end of which is located in an alcohol sensing chamber. The end of the tubular member in the chamber is closed. It s opposite end is open and it is provided with a pair of through-holes or vias in the wall thereof. A pressure transducer is coupled to a first one of the through-holes for measuring the pressure in the interior of the tubular member as a person blows a breath sample into the tubular member through the open end. The second through-hole is provided for passing the breath sample from the tubular member into the chamber. A sensor is located in the chamber for measuring the alcohol content of the breath sample. The diameter of the second through-hole, e.g. 0.1 inch, is chosen such that a person blowing a breath sample into the tubular member for about 7 seconds at a rate of flow of about 10 liters/minute will expel about one liter of air into the chamber. The pressure produced in the tubular member at that flow rate is about 6 inches of water. A liter of air insures that a deep lung sample is being provided.

In contrast to prior known breath analyzers, the flow rate integrator of the present invention allows for the production of usable breath samples over a relatively wide range of flow rates. For example, it is found that a deep lung sample is produced if the product of flow rate and time at and within which a sample is provided is approximately a predetermined constant for any combination of flow rate and time. Accordingly, if a person provides a breath sample at a flow rate of less than 10 liters/minute, the required length of time of the sampling is extended. Conversely, if the breath sample is provided at a flow rate of more than 10 liters/minute, the required length of time of the sampling is reduced.

In the servograph there is provided a plurality of seven lights, e.g. light emitting diodes (LED's), and a tone generator. The lights are located along a line adjacent to the above-described tubular member into which a breath sample is provided. The position of the lights is such that the person providing the breath sample is able to view the lights while giving the sample.

The purpose of the servograph is to ensure that the air sample is being given by a human subject and not through the use of a pre-filled balloon, air pump or the like.

As indicated above, the servograph consists of a line of seven lights, e.g. LEDs. The lights located in positions #1 and #7 are red; #2, #3, #5 and #6 are yellow; and #4 is green. A green light located adjacent to the other lights indicates that a TEST can be taken and is not part of the servograph.

In operation, the operator must initially provide the breath sample at a rate of flow sufficient to turn on the green light located in position #4. Thereafter, the device will vary the rate of flow required to keep the green light on. When either the #2 or #3 yellow light turns on, the operator must increase the flow rate to turn on the green light. When either the #5 or #6 yellow light turns on, the operator must decrease the flow rate to again turn on the green light. Each time that a #2 or #3 yellow light turns on, the sample period is extended and each time a #5 or #6 yellow light turns on, the sample period is reduced so that a deep lung sample can be produced even when the flow rate varies. If either of the red lights #1 or #7 turn on for more than a short period, e.g. one second, then the operator must start the test over again. Audible signals will be produced when the various lights are turned on.

The flow rate required to turn on the various lights is automatically changed by means of a microprocessor during the delivery of a breath sample and from one test to the next. Thus, only a human subject will be capable of adjusting the flow rate while visually observing the servograph lights.

Function/mode lights are provided to indicate to the operator when the system is ready to be used for a test (TEST), the operator has failed the test (LOCK), or has passed the test (START). A function light (PAUSE) is illuminated when the system is being readied for a test. A function light (SERVICE) is illuminated when the system is due for a calibration or when tampering has been detected.

A further advantage of the present invention is that a number of the system components including the gas sensor, flow sensor and a non-volatile memory are placed in a replaceable calibration module to facilitate field calibration, repair and/or replacement.

BRIEF DESCRIPTION OF THE DRAWINGS

The above and other objects, features and advantages of the present invention will become apparent from the following detailed description of the accompanying drawings, in which.

DETAILED DESCRIPTION OF THE DRAWINGS

In the following description of the drawings, like elements in each of the figures will be identified by the same numerical and/or alphabetical designator. The electronic and other components of the present invention are generally found in one of three modules, i.e. a processor module P, a sensor module S and a replaceable calibration module C. The processor module P is typically mounted under the dashboard of a vehicle. The sensor module S and replaceable calibration module C are located in a handset, as will now be described. The components in each of these modules are designated by the letters P, S and C, respectively.

Referring to FIGS. 1-6, there is provided in accordance with the present invention an L-shaped handset designated generally as 1 comprising a long section 2 and a short section 3. In the upper middle portion of the long section 2 there is provided five function lights S2 designated specifically LOCK, START, PAUSE, TEST and SERVICE, respectively. In the short section 3 there is provided a plurality of servograph lights designated generally as C6. To the right of lights C6 there is provided a hole 5. Above the hole 5 there is shown a disposable mouthpiece 7. Mouthpiece 7 comprises a generally rectangular body member 9 and a pair of identical tapered tubular members 10 and 11 extending from opposite ends thereof. As will be further described below, is use, one of the ends 10 and 11 is inserted in the hole 5 while the other end serves as a mouthpiece.

Figure 1:
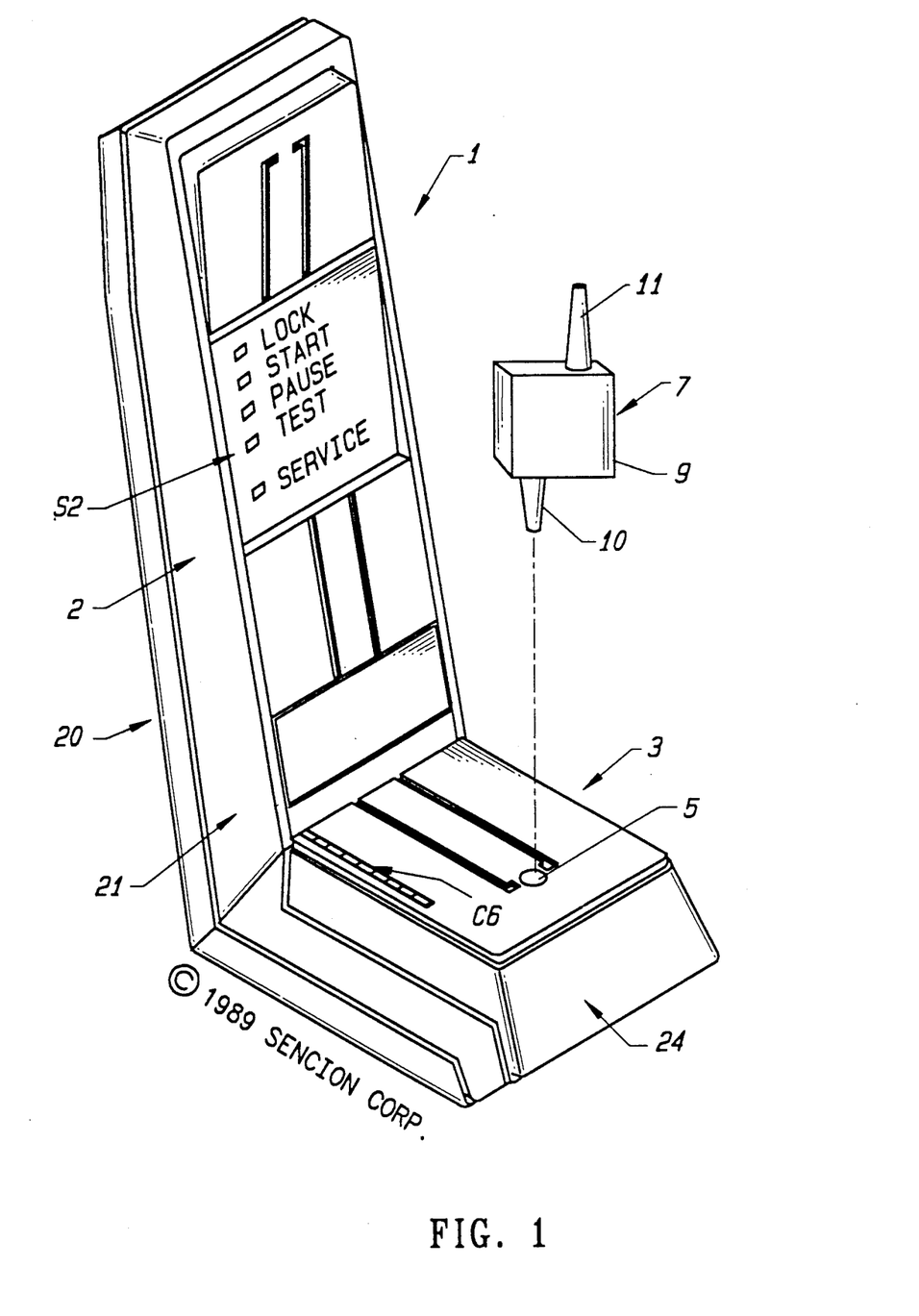
FIG. 1 is a perspective view of a handset in a vehicular ignition interlock system according to the present invention.
Figure 2:
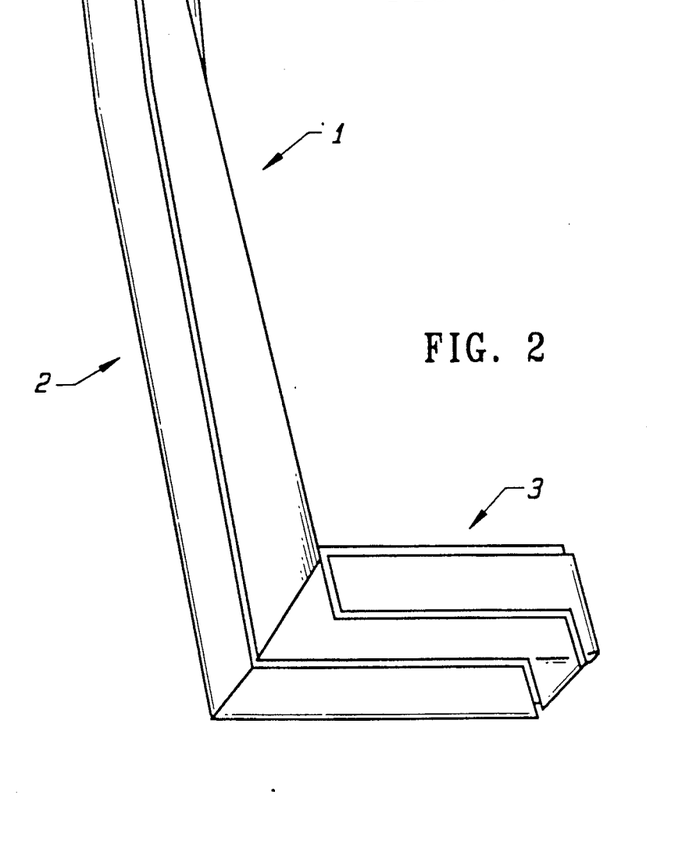
FIG. 2 is a side elevation view of the handset of FIG. 1.
Figure 3:
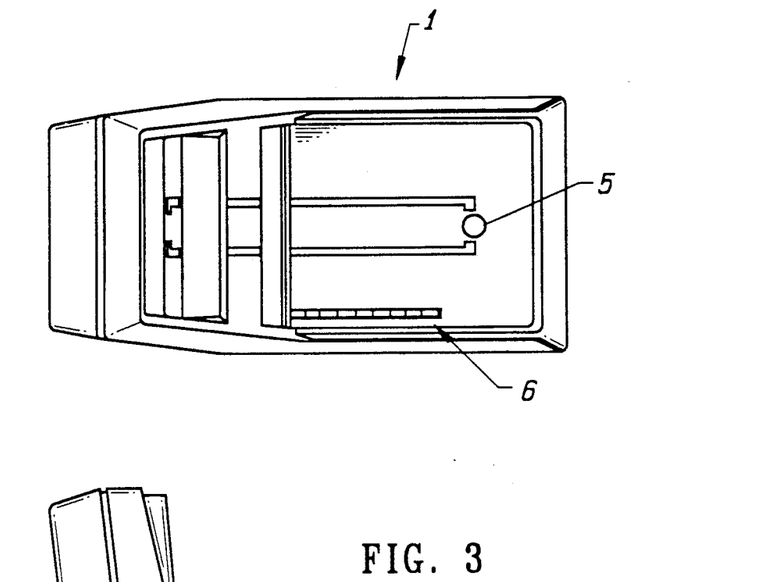
FIG. 3 is a top plan view of FIG. 2.
Figure 4:
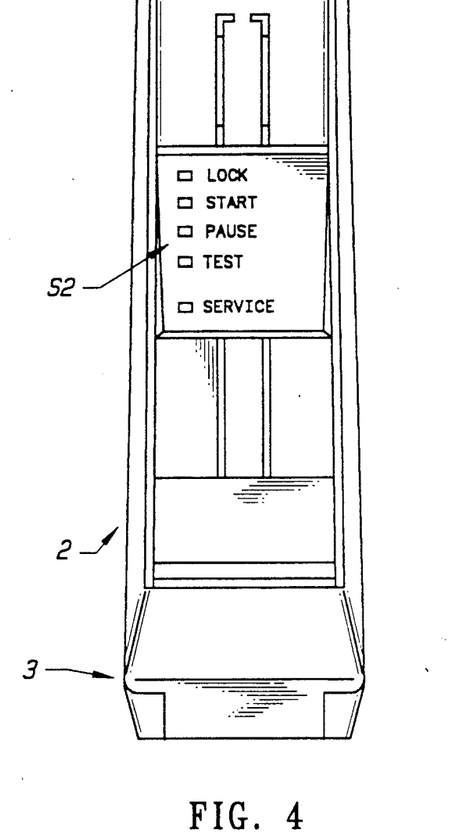
FIG. 4 is a front elevation view of FIG. 3.
Figure 5:
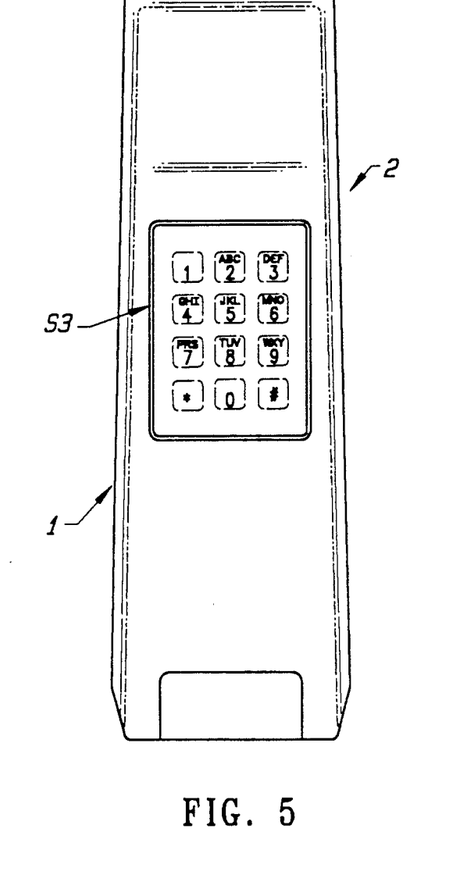
FIG. 5 is a rear view of FIG. 4.

As shown in FIG. 5, there is provided in the center of the rear of the long section 2 a key pad S3 comprising a plurality of alpha/numeric keys identical to those found on a conventional telephone. The keypad S3 is provided for entering data and codes into the system.

Figure 6:
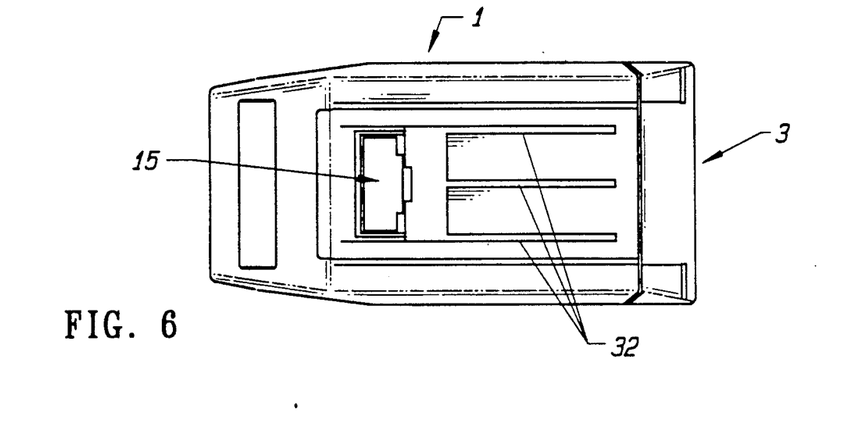
FIG. 6 is a bottom plan view of FIG. 5.

Referring to FIG. 6, there is provided in the bottom rear of the short section 3 a connector designated generally as 15. Connector 15 is provided, in conjunction with a cable, not shown, for connecting the sensor module S and replaceable calibration module C in the handset 1 to the processor module P mounted under the dashboard.

Figure 7:
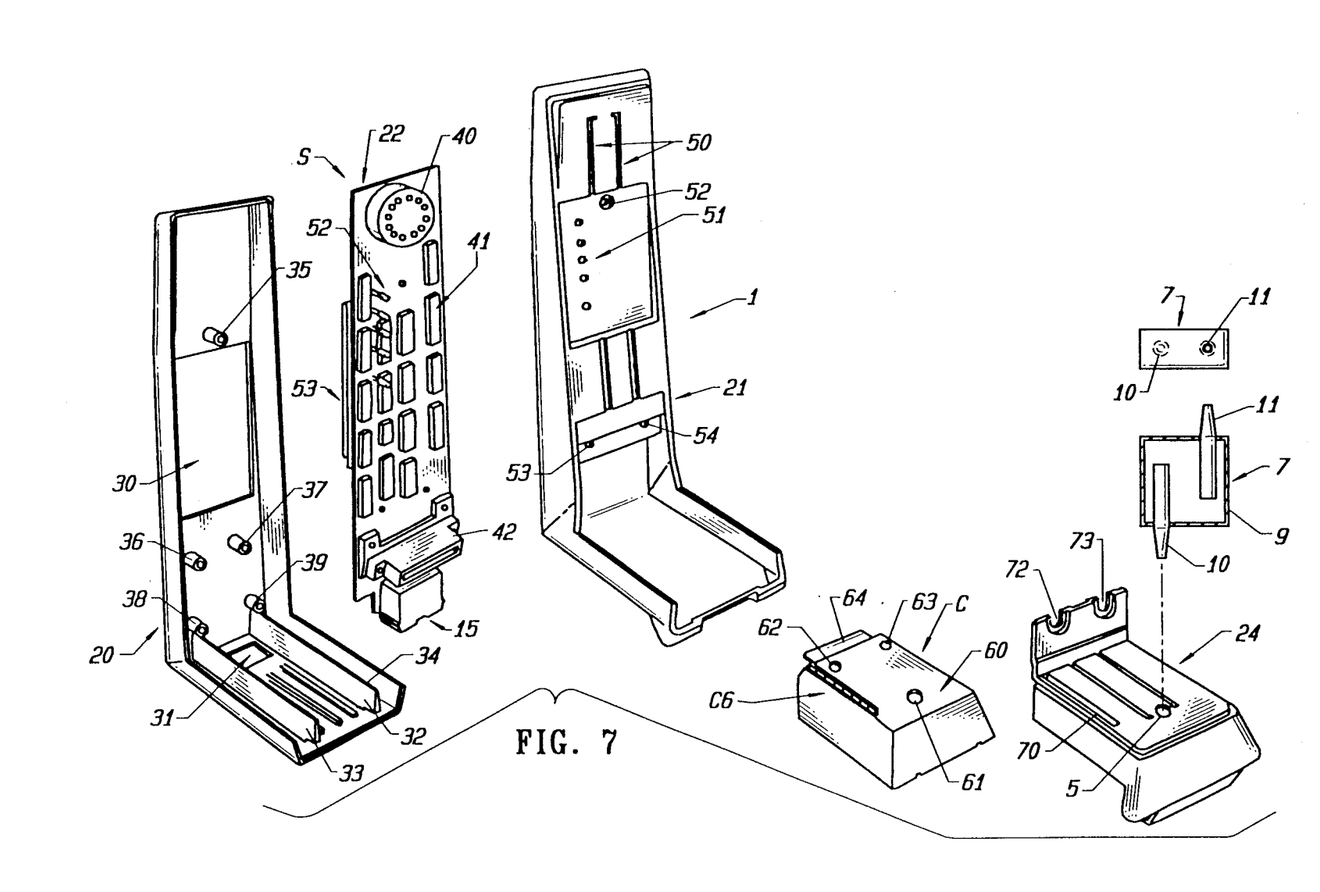
FIG. 7 is an exploded view of the handset of FIGS. 1-6.

Referring to FIG. 7, there is provided in the handset 1 a rear/bottom cover 20, a front cover 21, an electronic circuit assembly 22, the replaceable calibration module C and a top cover 24. In the center of the rear panel of the rear/bottom cover 20 there is provided a hole 30 for receiving the keypad S3, a hole 31 for receiving the connector 15 and a plurality of slots 32. Slots 32 permit the exhausting of breath samples from the replaceable calibration module C as will be further described below. On opposite sides of the slots 32 there is provided a pair of rails 33 and 34. In the rear section of the back cover 20 there is provided a plurality of mounting posts 35, 36, 37, 38 and 39.

In the assembly 22 there is provided at the top thereof a speaker 40. Below the speaker 40 there is provided a plurality of electronic integrated circuits 41 which make up the sensor module S. Along the left side of the circuits 41 there is provided the five function lights, e.g. LED's S2. At the lower end of the assembly 22 provided another electrical connector 15 there is provided another electrical connector 42 for connecting the replaceable calibration module C to the sensor module S. As can be seen, the keypad S3 is mounted on the back of the assembly 22 and the electrical connector 15 is mounted at the bottom of the assembly 22.

Referring to the front cover 21, there is provided at the upper end thereof a plurality of slots 50 through which sound from the speaker 40 emanates. Below the slots 50 there is provided a recessed area in which is provided a plurality of holes 51 for receiving the function lights S2. Above and to the right of the holes 51 there is provided a hole 52. Below the function light holes 51 there is provided a pair of holes 53 and 54. Holes 52, 53 and 54 are provided for mounting the front cover 21 and electronic assembly 22 to the posts 35, 36 and 37 of the rear/bottom cover 20 as by conventional screws. With the assembly 22 mounted on the posts 35, 36 and 37, the keypad S3 projects through the hole 30 and the electrical connector 15 is accessible through the hole 31.

In the replaceable calibration module C, as will be further described below, there is provided a top cover 60, the servograph lights C6 and a hole 61. At the rear of the cover 60 there is provided a pair of mounting holes 62 and 63. Extending from the rear of the module C there is provided a male electrical connector 64.

In the top cover 24 there is provided a slot 70 and the hole 5 and a pair of open-ended holes 72 and 73. The slot 70 is provided for receiving the servograph lights C6. The hole 5 is provided to be in registration with the hole 61 for receiving the tubular member 10 of the mouthpiece 7.

As seen in FIG. 7, the body member 9 of the disposable mouthpiece 7 comprises a hollow rectangular body member into which the tubular members 10 and 11 project. As so constructed, the body member 9 serves as a saliva trap which prevents saliva from being blow into the replaceable calibration module during a breath test.

Referring to FIGS. 8-11, there is provided in the replaceable calibration module C a bottom cover 80 having a plurality of slots 81, an upstanding support member 82, a pair of rail receiving slots 83 and 84, a pair of mounting posts 85 and 86, a bottom wall 87 and a rear wall 88. Slots 81 are provided for exhausting breath samples from the replaceable calibration module C through the slots 32 in the rear/bottom cover 20 described above with respect to FIG. 7. The slots 83 and 84 are provided for supporting the replaceable calibration module C on the rails 33 and 34, respectively, of the rear/bottom cover 20 described above with respect to FIG. 7. The support 82 and the mounting posts 85 and 86 are provided for supporting a circuit board 90.

Figures 8, 9, 10, 11:
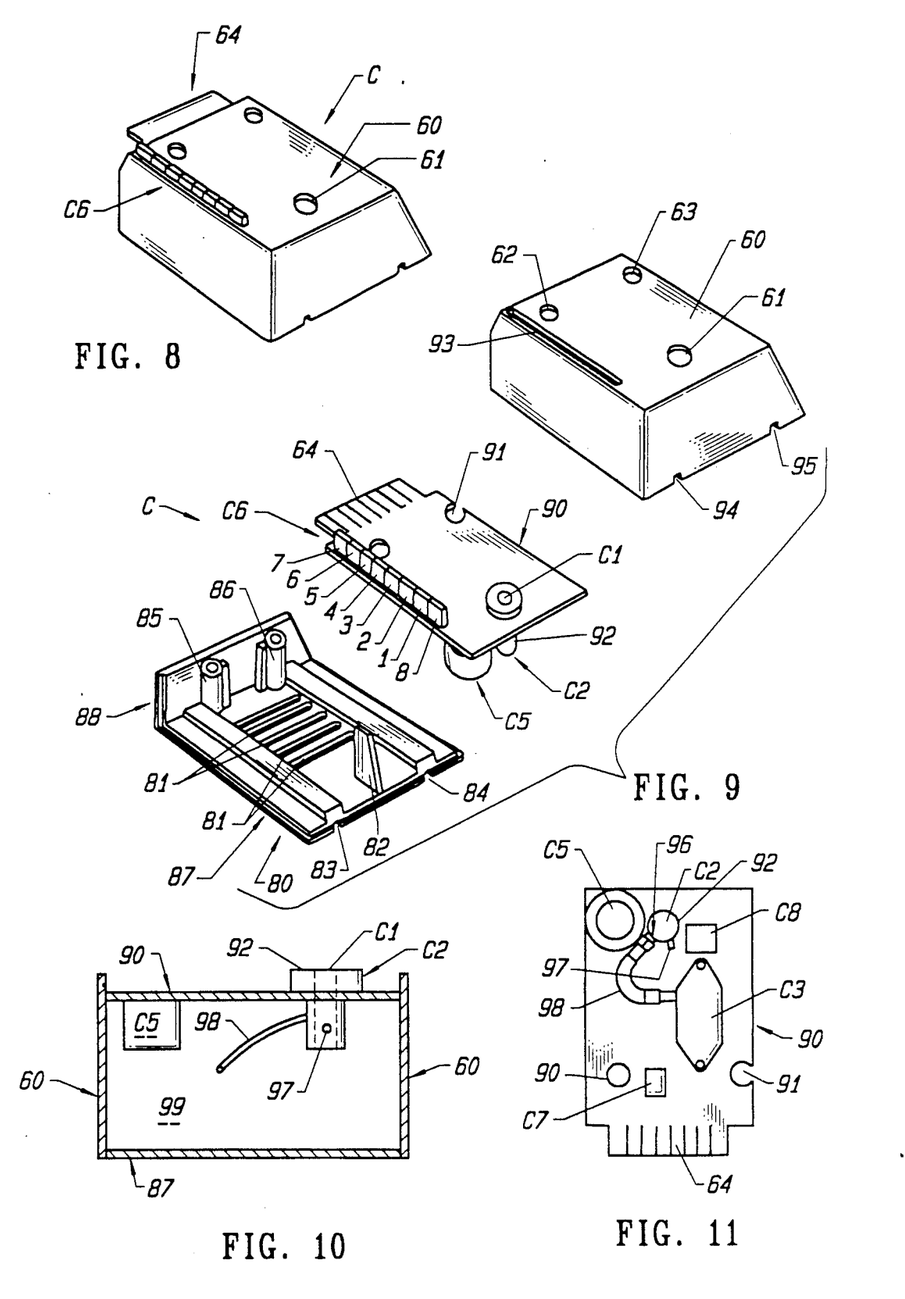
FIG. 8 is a perspective view of the replaceable calibration module of FIG. 7.
FIG. 9 is an exploded view of the replaceable calibration module of FIG. 8.
FIG. 10 is a partial cross-sectional view showing the chamber in the replaceable calibration module of FIG. 8.
FIG. 11 is a bottom plan view of the circuit board in the replaceable calibration module of FIG. 9.

In the circuit board 90 there is provided a pair of mounting holes 90 and 92 for mounting the board 90 to the posts 85 and 86. The male electrical connector 64 extends to the rear of the mounting holes 90 and 91. At the forward end of the board 90 there is provided a breath flow rate assembly C2 comprising a tubular member 92 having a breath inlet port C1. To the left of the tubular member 92 there is provided a breath gas sensor C5. Along the left edge of the board 90 there is provided the seven servograph lights C6. For convenience, the lights C6 are individually identified from front to back with the numbers 1-7. As will be further described below, light 4 is green, lights 1 and 7 are red and lights 2, 3, 5 and 6 are yellow. Light 8, which is also green is a TEST light, corresponding to the TEST function light on the front panel of the handset and is not a part of the servograph.

In the cover 60 there is provided as described above the hole 61, the holes 62 and 63, a slot 93 for receiving the lights C6 and a pair of slots 94 and 95 corresponding to the slots 83 and 84 in the bottom member 80.

When the board 90 is mounted on the support 82 and secured to the posts 85 and 86 together with the cover 60, a test chamber 99, as shown in FIG. 10, is formed. The test chamber 99 is formed by the board 90, the side walls of the cover 60 and the bottom and rear walls 87 and 88 of the bottom cover 80.

Referring to FIGS. 10 and 11, the end of the tubular member 92 in the test chamber 99 is closed. In the walls of the tubular member 92 there is provided a first hole 96 and a second hole 97. Extending down from the bottom of the board 90 and mounted thereto, there is provided a Taguchi gas sensor C5, a flow sensor C3, a voltage regulator C8 for regulating the voltage applied to the sensor C5, and a non-volatile memory C7 for storing the calibration parameters of the sensors C3 and C5. The flow sensor C3 comprises a pressure transducer which is connected to the hole 96 by means of a flexible tubular member 98 for measuring the pressure of a breath sample in the interior of the tubular member 92. The diameter of the second hole 97 is approximately 0.1 inch for producing a pressure of about 6 inches of water in the tubular member 92 when the rate of flow through hole 97 is about 10 liters/minute. While the hole 97 is shown as comprising a member extending from the tubular member 92, in a preferred embodiment of the present invention it is simply a through-hole in the wall of the tubular member 92 which allows the passage of a breath sample from the interior of the tubular member 92 to the sensor C5 in the chamber 99. The placement of the assembly C2, sensors C3, C4 and C5, servo LED's C6, memory C7 and regulator C8 in the replaceable calibration module C facilitates field calibration and repair of the system.

Figure 12:
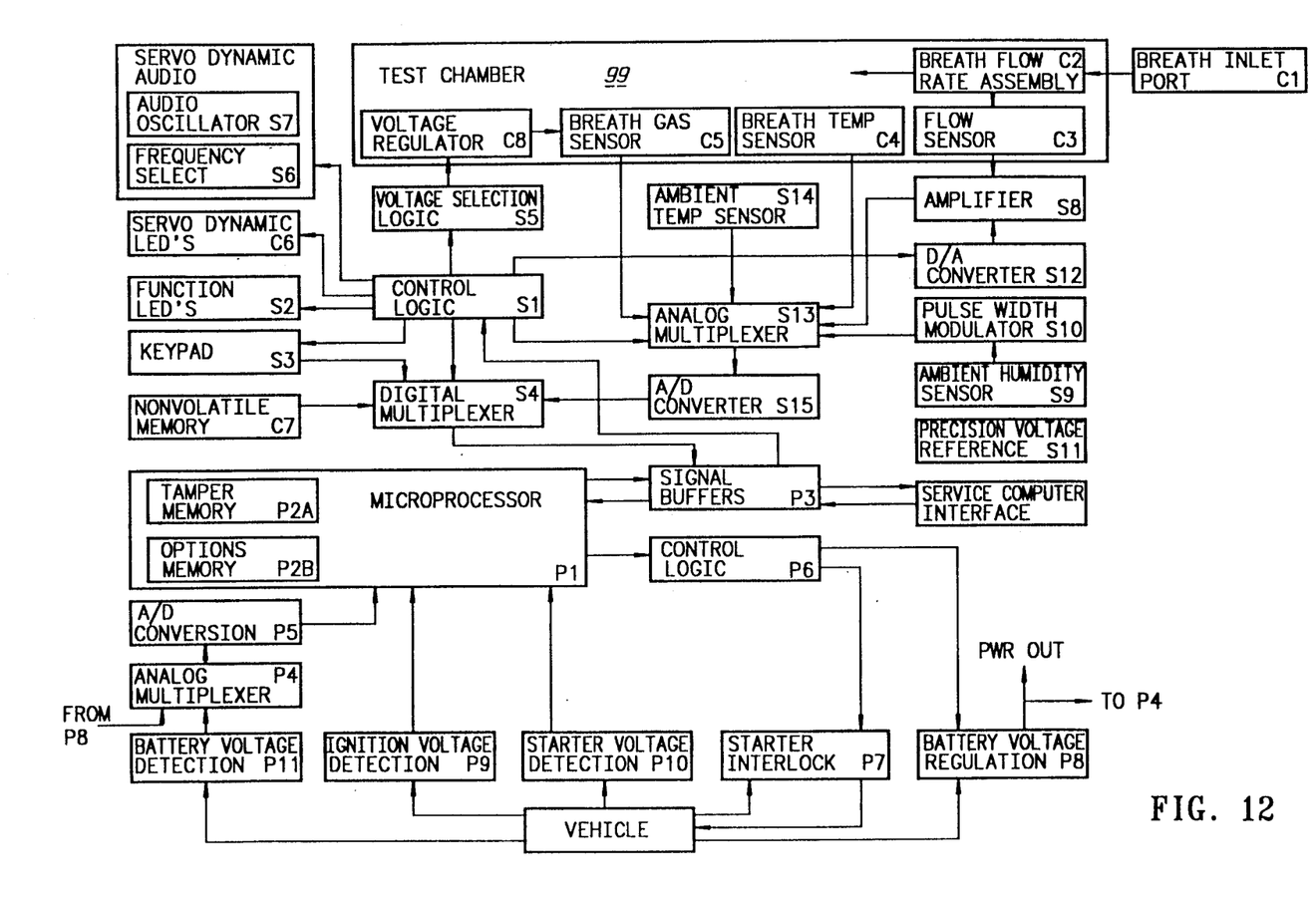
FIG. 12 is a block diagram of a vehicular ignition interlock system according to the present invention.

Referring to FIG. 12, as previously discussed, the vehicular ignition interlock system of the present invention generally comprised a processor module P, a sensor module S and a replaceable calibration module C. Each of the component parts of the processor module are designated by the letter P, each of the component parts of the sensor module are designated by the letter S and each of the component parts of the replaceable calibration module are designated by the letter C.

In the processor module P there is provided a microprocessor P1, a tamper memory P2A, an options memory P2B, an input/output signal buffer P3, an analog multiplexer P4, an A/D converter P5, a control logic circuit P6, a starter interlock circuit P7, a battery voltage regulation circuit P8, an ignition voltage detection circuit P9, a starter voltage detection circuit P10 and a battery voltage detection circuit P11.

In the microprocessor P1 there is provided an integrated computer on a chip that controls all process functions and monitors sensor activity, making determinations based on predetermined calibration set points which are provided by the factory.

In the tamper memory P2A there is provided a non-volatile memory for storing the following events and/or data:

(a) each breath test result (pass or fail);

(b) each roll start occurrence which happens when an attempt is made to start the automobile as by rolling it down a hill or having it pushed by another vehicle;

(c) each hot wire incident as occurs when an attempt is made to start the car by shorting the starter solenoid;

(d) each battery low condition which results in an automatic power shutdown;

(e) each emergency start which occurs when a secret/auxiliary code is used to bypass the ignition interlock system in order to get the vehicle started in an emergency;

(f) each disconnect or malfunction of the replaceable calibration module;

(g) the date and time of each of the above-listed events;

(h) the ambient temperature and humidity;

(i) background conditions such as produced by ambient gas fumes, methanol, paint thinner, etc.

(j) serial number of each module;

(k) a listing of factory programmed optional features, if any.

In the options memory P2B there is provided a nonvolatile memory which stores the following information:

(a) Blood alcohol concentration (BAC) threshold level. For example, in California the legal BAC threshold level is 0.08 BAC. The threshold level set for the ignition interlock system of the present invention is 0.03 BAC.

(b) Emergency override. This is the secret code used for emergency starts described above under subparagraph (e) in the description of the tamper memory P2A.

(c) Recalibration frequency. This is the number of days between recalibrations of the ignition interlock system. Depending upon the state in which the system is used, the time may be, for example, 60 to 90 days. One of the function lights, namely the SERVICE light, is illuminated 7 days ahead of the calibration deadline so as to advise the operator of the need to obtain a recalibration of the system. At the end of the 7 days, the system automatically shuts down.

In the input/output signal buffer P3, there is provided a plurality of bidirectional inverters for buffering signals to and from the microprocessor P1 via interconnecting cables.

In the analog mulitplexer P4 there are provided two inputs and an output coupled to the A/D converter P5. One of the inputs is coupled to the output of the battery voltage detection circuit P11 and another input is coupled to an output of the battery voltage regulation circuit P8.

In the A/D converter P5 there is provided a means for converting the analog outputs from the battery voltage detection circuit P11 and the battery voltage regulation circuit P8 to digital signals for use by the microprocessor P1.

In the control logic P6 there is provided a plurality of microprocessor controlled latched used for controlling the starter interlock P7 and battery voltage regulation circuit P8.

In the starter interlock circuit P7 there is provided a relay which is controlled by the control logic circuit P6 for allowing current to be applied to the vehicle starter when the operator has passed the alcohol breath test.

In the battery voltage regulation circuit P8 there is provided a voltage regulation circuit which is turned on and off by the control logic to disable power to the ignition interlock system when low input voltages are detected, so as not to damage the system. The circuit P8 provides power to all of the system's electronic components.

In the ignition voltage detection circuit P9 there is provided a circuit for detecting whether the vehicle ignition key is in its ON or OFF position.

In the starter voltage detection circuit P10 there is provided a circuit for detecting when power is applied to the starter to determine if a "hot wire start" tamper has occurred.

In the battery voltage detection circuit P11 there is provided a circuit for detecting the battery voltage level of the vehicle. The ignition interlock system of the present invention is shut down when low voltage is detected. An engine running condition can also be detected indicating that a "roll start" tamper has occurred.

The components of the sensor module are designated by the letter S. In the sensor module there is provided a control logic circuit S1, the plurality of function light emitting diodes (LED's) S2, the keypad S3, a digital multiplexer S4, a voltage selection logic circuit S5, a frequency select circuit S6, an audio oscillator S7, an amplifier S8, an ambient humidity sensor S9, a pulse width modulator S10, a precision voltage reference circuit S11, a D/A converter S12, an analog multiplexer S13, an ambient temperature sensor S14 and an A/D converter S15.

In the control logic circuit S1 there is provided a plurality of circuits controlled by the microprocessor P1 to select the function LED's S2, the illumination of the servograph display LED's C6, the keypad S3 and discrete sensor outputs from the breath gas sensor C5, the ambient temperature sensor S14, a breath temperature sensor C4, as will be further described below, the flow sensor C3 via the amplifier C8 and the ambient humidity sensor S9 via the pulse width modulator S10, all of these signals being routed through the analog multiplexer S13 to the A/D converter S15, the digital multiplexer S4 and the signal buffers P3 to the microprocessor P1.

In the function LED's S2, as previously discussed, there is provided a number of light emitting diodes which act as an interface to the operator including:

(a) LOCK which is illuminated to indicate a failed breath test. The illumination comprises a steady red light and beeping multi-mid-frequency warbling tones, which lasts for approximately 20 seconds. At the end of the 20 second period the system goes to the PAUSE mode and then to the TEST mode, as will be further described below.

(b) START which is illuminated when the operator passes the breath test. The start light is a steady green light and is accompanied by beeping multi-mid-frequency melodious tones which are generally more pleasant to hear than the LOCK tones.

(c) PAUSE mode comprises a wait indication. The light illuminated is an amber light which is unaccompanied by any tone and lasts for approximately one minute. During this period, control logic S1 increases the voltage applied to the breath gas sensor C5 via the voltage selection logic S5 and the voltage regulator C8 in order to raise the temperature of the breath gas sensor so as to purge the breath gas sensor C5 of contaminants, such as gas fumes, methanol, paint thinner, alcohol from prior breath test, etc.

(d) TEST mode indicates that the system is ready for a breath sample. It is indicated by a steady green light unaccompanied by a tone. During the test, as will be further described below, the servograph LED lights and tones are used by the operator.

(e) SERVICE indicates that less than n days, e.g. 7 days, remains before service is required. A blinking red light is illuminated without an accompanying tone.

In the keypad S3 there is provided a plurality of keys for entering operator programmable options into the device such as the emergency start authorization code, a manual shutdown which is used, for example, if the system is not going to be used for a long period of time, audio tone volume control and a personal identification number.

In the digital multiplexer S4 there is provided a plurality of inputs for receiving the outputs from the keypad S3, the non-volatile memory C7 and the A/D converter S12 under control of the microprocessor P1 via the logic circuit S1.

In the voltage selection logic circuit S5 there is provided a means for selecting the heater voltage level for the gas sensor which changes the temperature of the gas sensor from a typical operating temperature of 150° C. to 300° C. to about 350° C. in order to purge the gas sensor of contaminants.

In the frequency select circuit S6 there is provided a means controlled by the microprocessor P1 via the control logic circuit S1 to establish the frequency of the audio oscillator S7 so as to provide low, mid and high tones during the operation of the servograph.

In the audio oscillator S7 there is provided a means for driving the speaker in order to produce the various tones in a conventional manner.

In the amplifier S8 there is provided an input for receiving the output of the flow sensor C3 and an input for receiving a bias level input signal from the D/A converter S12.

In the ambient humidity sensor S9 there is provided a variable capacitance device which measures the relative humidity of the ambient air.

In the pulse width modulator S10 there is provided a means for developing an analog signal proportional to the humidity by modulating and detecting an oscillator frequency in response to an output from the ambient humidity sensor S9.

In the precision voltage reference circuit S11 there is provided a means for developing a stable voltage which is used by the analog circuitry for accuracy.

In the D/A converter S12 there is provided a means for applying a bias to the amplifier circuit S8 to produce a zero air flow reference prior to each test. The bias is generated by automatically adjusting the bias to produce a predetermined output from the amplifier S8 with a zero air flow input from sensor C3.

In the analog mulitplexer circuit S13 there is provided a means for multiplexing analog signals received from the breath gas sensor C5, the breath temperature sensor C4, the flow sensor C3 via the amplifier S8 and the ambient humidity sensor S9 via the pulse width modulator S10 under the control of the logic circuit S1. The output of the analog multiplexer S13 is coupled to the A/D converter S15 for transmission to the microprocessor P1 via the digital multiplexer S4 and the signal buffer P3.

In the ambient temperature sensor S14 there is provided a thermistor with a long time constant which detects the ambient air temperature and sends the output to the analog multiplexer S13.

In the A/D converter S15 there is provided a means for converting the analog signals from the analog multiplexer S13 to a digital format for use by the microprocessor P1.

In the replaceable calibration module C there is provided the breath inlet port C1, the breath flow assembly C2, the flow sensor C3, the breath temperature sensor C4, the breath gas sensor C5, the servograph dynamic LED's C6, the non-volatile memory C7 and the voltage regulator C8.

In the breath inlet port C1 there is provided a sample input to the breath flow rate assembly C2. In operation, the disposable mouthpiece 7 is inserted into this port and the subject exhales breath through the mouthpiece into the breath flow assembly C2.

In the breath flow assembly C2 which comprises the tubular member 92, a portion of the sample is passed through the test chamber inlet port 97 and the other portion of the sample is passed through the tube 98 into the flow sensor C3.

In the flow sensor C3 there is provided a sensor which, in combination with the orifice, i.e. port 97, is calibrated to measure the flow rate so as to provide for a given pressure in the tubular member 92 and a breath sample of a predetermined duration, a deep lung sample corresponding to a flow rate of 10 liters per minute.

In the breath temperature sensor C4 there is provided a thermistor with a short time constant that measures the breath temperature. The thermistor is located in a space provided therefor in the tubular member 92 in the breath flow rate assembly C2.

In the breath gas sensor C5 there is provided a Taguchi gas sensor which produces a variable resistance as a function of ethanol concentration in the test chamber 99.

In the servograph LED's C6 there are provided the seven LED lights. The lights located in positions #1 and #7 are red, #2, #3, #5 and #6 are yellow and #4 is green. The green light located in position #8 will indicate a test condition and is not part of the servograph. As will be described, the lights are illuminated under the control of software by the microprocessor P1, by the signal buffer P3 and control logic S1.

In non-volatile memory C7 there is provided a means for storing the calibrator module parameters such as gas sensor calibrator values, flow sensor values, serial number and calibration date.

In the voltage regulator C8 there is provided a means selectable y the microprocessor P1 for setting the gas sensor heater levels in its normal and purge modes.

The operation of the ignition interlock system according to the present invention will now be described.

As previously discussed, the ignition interlock system of the present invention comprises five modes of operation, namely LOCK, START, PAUSE, TEST and SERVICE. When the system is in its LOCK mode, the LOCK LED which comprises a steady red light is illuminated and beeping multi-mid-frequency warbling tones are generated. When the system is in its START mode, the START LED comprising a steady green light is illuminated and different beeping multi-mid-frequency tones are generated which are generally more pleasant to heat than the LOCK tones. When the system is in its PAUSE mode, the PAUSE LED light comprising a steady amber light is illuminated. When the system is in its TEST mode, a TEST LED light comprising a steady green light is illuminated. When the system is in its SERVICE mode, the SERVICE LED light comprising a blinking red light is illuminated. In the PAUSE, TEST and SERVICE modes no tone is generated.

Under normal operation when the vehicle is at rest, i.e. not running, the ignition interlock system continues to operate, measuring and storing ambient temperature and humidity and continuously purging the alcohol sensor C5 of contaminants so that it is ready to make a BAC test as soon as the operator turns on the ignition.

Upon entering the vehicle, the operator inserts one of the tubular members 10, 11 of the mouthpiece 7 in the breath inlet port C1 and turns on the ignition. Upon turning on the ignition, the ignition interlock system of the present invention enters its TEST mode as indicated by a steady green light on the long section 1 and the #8 green light on the short section 3 of the handset 1. The steady green lights indicate that the system is ready for a breath sample. Upon noting the green lights, the operator exhales into the mouthpiece 7 while observing the servograph lights C6 on the short section 3 of the handset 1. As previously discussed, the lights located in positions #1 and #7 are red, the lights located in positions #2, #3, #5 and #6 are yellow and the light located in position #4 is green. As indicated above, the green light located in position #8 is another TEST light corresponding to the TEST light on the function panel and is illuminated with the TEST light on the function panel and is therefore not a part of the servograph.

To insure a deep lung sample, the operator must initially exhale at a rate of flow sufficient to turn on the green light located in position #4. Thereafter, the system is programmed to vary the rate of flow required to keep the green light in position #4 on. When either the #2 or the #3 yellow light turns on, the operator must increase the flow rate to turn on the green light. When either the #5 or the #6 yellow light turns on, the operator must decrease the flow rate in order to again turn on the green light. Each time that a #2 or #3 yellow light turns on, the sample period is extended and each time a #5 or #6 yellow light turns on, the sample period is reduced so that a deep lung sample can be produced even when the flow rate varies. If either the #1 or the #7 red light turns on for more than a short period, e.g. 1 second, then the operator must start the test over. The #1 red light turns on when the flow rate is too low to provide a deep lung sample within the period allowed. The #7 red light turns on to prevent the operator from using a flow rate which will cool the gas sensor C5 and affect the accuracy of the test. Audible signals are produced when the various lights are turned on to facilitate the operator in taking the test.

The flow rate required to turn on the various lights is automatically changed by the microprocessor P1 such that the flow rate necessary to turn on the green light #4 will vary during each test and from one test to the next. This is to insure that only a human subject will be capable of adjusting the flow rate while visually observing the servograph lights. The lights, their color, their condition and the tones generated when they are illuminated are as follows.

| LIGHT | COLOR | CONDITION/TONE |
| --- | --- | --- |
| #7 | red | Steady light/beeping hi-tone |
| #6 | yellow | Steady light/steady hi-tone |
| #5 | yellow | Steady light/steady mid-tone |
| #4 | green | Steady light/steady mid-tone |
| #3 | yellow | Steady light/steady mid-tone |
| #2 | yellow | Steady light/steady low-tone |
| #1 | red | Steady light/beeping low-tone |
| #8 | green | TEST (equivalent to front panel and not actually part of the servograph |

If the operator fails to provide a deep lung sample in the manner described above, the system will re-enter its TEST mode to enable immediate retesting if no alcohol is detected or its PAUSE mode to purge the gas sensor C5 if alcohol is detected. The tones associated with the illumination of the #1 and #7 red lights are generated after the #1 and #7 lights have been illuminated for about one second to indicate to the operator that the test must be repeated. If the operator provides the required deep lung sample and less than the threshold level of alcohol is detected, the system will enter its START mode. On the other hand, if alcohol at or above the threshold is detected, the system enters its LOCK mode. In its LOCK mode a steady red light is illuminated on the function panel and the above-described beeping multi-mid-frequency warbling tones are generated. The LOCK mode lasts for approximately 20 seconds and the system then re-enters it PAUSE mode.

The PAUSE MODE is indicated by the illumination of a steady amber light on the long section 2 of the handset 1. In the PAUSE mode which lasts for about one minute, the microprocessor P1 sends a signal via the signal buffer P3 and the control logic S1 to the voltage selection logic circuit S5. The output of the voltage selection logic circuit S5 sends a control signal to the voltage regulator C8 which increases the breath gas sensor C5 to a temperature of about 350° C. to purge the breath gas sensor C5 of contaminating gases. At the end of the PAUSE mode the system enters its TEST mode in preparation for receiving another breath sample.

If the system has been shut down for a length of time either manually or automatically, it will enter its PAUSE mode when the operator turns on the ignition so as to insure an accurate BAC test.

While a preferred embodiment of the present invention is described above, it is contemplated that various modifications may be made thereto without departing from the spirit and scope thereof. Accordingly, it is intended that the embodiment described by considered only as an illustration of the present invention and that the scope thereof should not be limited thereto but be determined by reference to the claims hereinafter provided and their equivalents.

What is claimed is:

1. In an ignition interlock system, an apparatus for measuring the alcohol concentration of breath sample, comprising:
    means for receiving said breath sample from a person exhaling into said receiving means;
    means for measuring the rate of flow of said breath sample while said breath sample is being exhales by said person into said receiving means;
    means responsive to said rate of flow measuring means for indicating to said person the length of time that said person must exhale into said receiving means so as to insure that said person provides a predetermined volume of said breath sample;
    means responsive to said rate of flow measuring means for extending said period of time when said rate of flow is below a selected magnitude and for reducing said period of time when said rate of flow is above said selected magnitude; and
    means located in said receiving means for measuring the alcohol concentration of said breath sample at the end of said period of time when said predetermined volume of breath sample has been received in said receiving means.

2. Apparatus according to claim 1 wherein said indicating means comprises a plurality of lights and means for selectively illuminating individual ones of said lights as a function of the magnitude of said rate of flow.

3. Apparatus according to claim 2 wherein said means for illuminating individual ones of said lights comprises means for varying the magnitude of said rate of flow at which each of said individual ones of said plurality of lights is illuminated so as to make it difficult to provide said breath sample by a means other than a person exhaling into said receiving means.

4. Apparatus according to claim 2 wherein said means for illuminating individual ones of said plurality of lights comprises means for illuminating a first one of said plurality of lights when said rate of flow is at said selected magnitude, a second and a third one of said plurality of lights when said rate of flow is below said selected magnitude and a fourth and a fifth one of said plurality of lights when said rate of flow is above said selected magnitude.

5. Apparatus according to claim 4 wherein said means for illuminating individual ones of said lights comprises means for varying the magnitude of said rate of flow at which each of said individual ones of said plurality of lights is illuminated so as to make it difficult to provide said breath sample by a means other than a person exhaling into said receiving means.

6. Apparatus according to claim 1 wherein said indicating means comprises a plurality of audible tones and means for selectively generating said tones as a function of said selected magnitude of said rate of flow.

7. Apparatus according to claim 1 wherein said selected magnitude of said rate of flow is nominally approximately 10 liters/minute and said period of time is nominally approximately 7 seconds.

8. Apparatus according to claim 1 wherein said predetermined volume is approximately 1 liter.

9. Apparatus according to claim 1 wherein said rate of flow measuring means comprises a flow sensor and said alcohol concentration measuring means comprises a gas sensor and further comprising:
 means for storing data usable for calibrating said flow sensor and said gas sensor; and
 means for mounting said flow sensor, said gas sensor and said storing means in a replaceable calibration module to facilitate field repair, replacement and calibration of said flow sensor and said gas sensor.

10. In an ignition interlock system, an apparatus for measuring the alcohol concentration of a breath sample comprising:
 means for receiving said breath sample;
 means for measuring the rate of flow and temperature of said breath sample in said receiving means as said breath sample is being delivered to said receiving means;
 means for providing a first indication when said rate of flow has a pre-selected magnitude;
 means for providing a second indication when said rate of flow is below said pre-selected magnitude;
 means for providing a third indication when said rate of flow is above said pre-selected magnitude, said second and said third indication providing means serving to direct the person providing said breath sample to make a corresponding change in the rate of flow of said breath sample being delivered to said receiving means so as to return said rate of flow to said pre-selected magnitude; and
 means for automatically changing said pre-selected magnitude at which said first indication is provided while said breath sample is being delivered so as to make it extremely difficult to provide said breath sample by a means other than a person exhaling into said receiving means.

11. An apparatus according to claim 10 wherein said means for providing said first, said second and said third indications comprises means for providing a first, second and third visual indication, respectively.

12. An apparatus according to claim 11 comprising means for generating a pre-selected tone with each of said first, said second and said third visual indications.

13. An apparatus according to claim 10 wherein said means for providing said first, said second and said third indications comprises means for providing a first, a second and a third audible indication, respectively.

14. An apparatus according to claim 10 wherein said means for providing said first, said second and said third indications comprises a line of seven lights, a first and a seventh one of said lights in said line comprising a red light, a second, a third, a fifth and a sixth one of said lights in said line comprising a yellow light and a fourth one of said lights in said line comprising a green light.

15. An apparatus according to claim 14 wherein said means for providing said first, said second and said third indications comprises means for illuminating one of said first, said second and said third lights when said rate of flow of said breath sample is below said pre-selected magnitude and one of said fifth, said sixth and said seventh lights when said rate of flow of said breath sample is above said pre-selected magnitude for providing a visual indication that the rate of flow of said breath sample to said receiving means should be increased and decreased, respectively, in order to change the rate of flow of said breath sample to said pre-selected magnitude and illuminate said fourth light.

16. An apparatus according to claim 15 comprising means for generating an intermittent low tone when said first light is illuminated, a steady low tone when said second light is illuminated, a steady mid-tone when said third, said fourth and said fifth lights are illuminated a steady high tone when said sixth light is illuminated and an intermittent high tone when said seventh light is illuminated.

17. An apparatus according to claim 10 wherein said breath sample receiving means comprises:
 a chamber; and
 a tubular member having a portion thereof extending into said chamber, an open end through which said breath sample is provided and a through-hole in a wall thereof for passing said breath sample to said chamber; and said rate of flow measuring means comprises:
 a pressure measuring means; and
 means for coupling said pressure measuring means to said tubular member for measuring the pressure of said breath sample therein for a period of time, the diameter of said through-hole being such that a breath sample being delivered to said tubular member at a predetermined pressure for a predetermined period of time will produce a deep lung breath sample in said chamber.

18. An apparatus according to claim 17 wherein said predetermined pressure is approximately 6 inches of water and said predetermined period of time is approximately 7 seconds.

19. An apparatus according to claim 17 wherein said diameter of said through-hole is approximately 0.1 inch.

20. An apparatus according to claim 10 having a plurality of modes of operation and further comprising:
 an L-shaped handset having along section and a short section;
 means for mounting said breath receiving means, said rate of flow and temperature measuring means and said means for providing said first, said second and said third indication of said rate of flow of said breath sample in said lower section;

means located in a front panel of said long section for indicating when said apparatus is in each of its modes of operation; and a multi-key keypad located in a rear panel of said long section for entering data in said apparatus.

21. An apparatus according to claim 20 wherein said modes of operation comprise a LOCK mode, a START mode, a PAUSE mode, and a TEST mode, and further comprising:

means for causing said apparatus to enter its TEST mode when said apparatus is ready to receive and measure the alcohol concentration of a breath sample delivered thereof;

means for causing said apparatus to enter its START mode to enable the starting of a machine controlled thereby when the alcohol concentration of a tested breath sample is below a predetermined threshold level;

means for causing said apparatus to enter its LOCK mode when the alcohol concentration of a tested breath sample is at or above said predetermined threshold level to prevent the starting of said machine;

means responsive to said apparatus being in its LOCK mode for causing said apparatus to enter its PAUSE mode for a predetermined length of time after a predetermined length of time in said LOCK mode, said apparatus including means for purging a gas sensor located therein of contaminants while in said PAUSE mode; and means for returning said apparatus to its TEST mode upon the termination of said PAUSE mode.

22. An apparatus according to claim 21 wherein said means for causing said apparatus to enter its LOCK mode comprises means for causing said apparatus to enter its LOCK mode when said rate of flow of said breath sample is either above or below said pre-selected rate of flow by a predetermined amount for a predetermined period of time.

23. An apparatus according to claim 22 wherein said predetermined period of time is approximately one second.

24. In an ignition interlock system having a breath sample receiving mean, a method of measuring the alcohol concentration of a breath sample comprising the steps of:

receiving said breath sample from a person exhaling into said receiving means;

measuring the rate of flow of said breath sample while said breath sample is being exhaled by said person into said receiving means;

indicating the length of time that said person must exhale into said receiving means so as to insure that said person provides a predetermined volume of said breath sample;

extending said period of time when said rate of flow is below a selected magnitude and reducing said period of time when said rate of flow is above said selected magnitude; and measuring the alcohol concentration of said breath sample at the end of said period of time when said predetermined volume of breath sample has been received in said receiving means.

25. A method according to claim 24 wherein said indicating step comprises the step of selectively illuminating individual ones of a plurality of lights as a function of the magnitude of said rate of flow.

26. A method according to claim 25 wherein said step of illuminating individual ones of said lights comprises the step of varying the magnitude of said rate of flow at which each of said individual ones of said plurality of lights is illuminated so as to make it difficult to provide said breath sample by a means other than a person exhaling into said receiving means.

27. A method according to claim 25 wherein said step of illuminating individual ones of said plurality of lights comprises the steps of illuminating a first one of said plurality of lights when said rate of flow is at said selected magnitude, a second and a third one of said plurality of lights when said rate of flow is below said selected magnitude and a fourth and a fifth one of said plurality of lights when said rate of flow is above said selected magnitude.

28. A method according to claim 27 wherein said step of illuminating individual ones of said lights comprises the step of varying the magnitude of said rate of flow at which each of said individual ones of said plurality of lights is illuminated so as to make it difficult to provide said breath sample by a means other than a person exhaling into said receiving means.

29. A method according to claim 24 wherein said indicating step comprises the step of selectively generating a plurality of tones as a function of the magnitude of said rate of flow.

30. A method according to claim 24 wherein said selected magnitude of said rate of flow is nominally approximately 10 liters/minute and said period of time is nominally approximately 7 seconds.

31. A method according to claim 24 wherein said predetermined volume is approximately 1 liter.

32. In an ignition interlock system, a method of measuring the alcohol concentration of a breath sample comprising the steps of:

providing a breath sample receiving means;

delivering said breath sample to said breath sample receiving means;

measuring the rate of flow and temperature of said breath sample in said receiving means as said breath sample is being delivered to said receiving means;

providing a first indication when said rate of flow has a pre-selected magnitude;

providing a second indication when said rate of flow is below said pre-selected magnitude;

providing a third indication when said rate of flow is above said pre-selected magnitude, said second and said third indication serving to direct the person providing said breath sample to make a corresponding change in the rate of flow of said breath sample being delivered to said receiving means so as to return said rate of flow to said pre-selected magnitude; and automatically changing said pre-selected magnitude at which said first indication is provided while said breath sample is being delivered so as to make it extremely difficult to provide said breath sample by a means other than a person exhaling into said receiving means.

33. A method according to claim 32 wherein said steps of providing said first, said second and said third indications comprises the steps of providing a first, second and third visual indication, respectively.

34. A method according to claim 33 comprising the step of generating a pre-selected tone with each of said first, said second and said third visual indications.

35. A method according to claim 32 wherein said steps of providing said first, said second and said third indications comprises the steps of providing a first, a second and a third audible indication, respectively.

36. A method according to claim 32 wherein said steps of providing said first, said second and said third indications comprises the step of selectively illuminating a line of seven lights, a first and a seventh one of said lights in said line comprising a red light, a second, a third, a fifth and a sixth one of said lights in said line comprising a yellow light and a fourth one of said lights in said line comprising a green light.

37. A method according to claim 36 wherein said steps of providing said first, said second and said third indications comprises the steps of illuminating one of said first, said second and said third lights when said rate of flow of said breath sample is below said pre-selected magnitude and one of said fifth, said sixth and said seventh lights when said rate of flow of said breath sample is above said pre-selected magnitude for providing a visual indication that the rate of flow of said breath sample to said receiving means should be increased and decreased, respectively, in order to change the rate of flow of said breath sample to said pre-selected magnitude and illuminate said fourth light.

38. A method according to claim 37 comprising the steps of generating an intermittent low tone when said first light is illuminated for about one second, a steady low tone when said second light is illuminated, a steady mid-tone when said third, said fourth and said fifth lights are illuminated, a steady high tone when said sixth light is illuminated and an intermittent high tone when said seventh light is illuminated for about one second.

39. A method according to claim 32 wherein said step of providing said breath sample receiving means comprises the steps of:
providing a chamber; and
providing a tubular member having a portion thereof extending into said chamber, an open end through which said breath sample is provided and a through-hole in a wall thereof for passing said breath sample to said chamber; and said step of measuring said rate of flow of said breath sample comprises the steps of:
measuring the pressure of said breath sample in said tubular member for a period of time, the diameter of said through-hole being such that breath sample being delivered to said tubular member at a predetermined pressure for a predetermined period of time will produce a deep lung breath sample in said chamber.

40. A method according to claim 39 wherein said predetermined pressure is approximately 6 inches of water and said predetermined period of time is approximately 7 seconds.

41. A method according to claim 39 wherein said diameter of said through-hole is approximately 0.1 inch.

42. A method according to claim 32 wherein said system has a plurality of modes of operation and further comprising the steps of:
providing an L-shaped handset having a long section and a short section;
mounting said breath receiving means, a means for measuring the rate of flow and temperature of said sample and a means for providing said first, said second and said third indication of said rate of flow of said breath sample in said lower section;
providing a means in a front panel of said long section for indicating when said system is in each of its modes of operation; and
providing a multi-key keypad in a rear panel of said long section for entering data in said apparatus.

43. A method according to claim 42 wherein said modes of operation comprise a LOCK mode, a START mode, a PAUSE mode, and a TEST mode, and further comprising the steps of:
causing said system to enter its TEST mode when said system is ready to receive and measure the alcohol concentration of a breath sample delivered thereto;
causing said system to enter its START mode to enable the starting of a machine controlled thereby when the alcohol concentration of a tested breath sample is below a predetermined threshold level;
causing said system to enter its LOCK mode when the alcohol concentration of a tested breath sample is at or above said predetermined threshold level to prevent the starting of said machine;
causing said system, in response to said system being in its LOCK mode, to enter its PAUSE mode for a predetermined length of time after a predetermined length of time in said LOCK mode for purging a gas sensor located therein of contaminants while in said PAUSE mode; and
returning said system to its TEST mode upon the termination of said PAUSE mode.

44. A method according to claim 43 wherein said step of causing said system to enter its TEST mode comprises the step of causing said system to enter its TEST mode when said rate of flow of said breath sample is either above or below said pre-selected pressure by a predetermined amount for a predetermined period of time.

45. A method according to claim 44 wherein said predetermined period of time is approximately one second.

* * * * *

UNITED STATES PATENT AND TRADEMARK OFFICE
CERTIFICATE OF CORRECTION

PATENT NO. : 5,020,628
DATED : June 4, 1991
INVENTOR(S) : ACHILLE M. BIGLIARDI et al It is certified that error appears in the above-identified patent and that said Letters Patent is hereby corrected as shown below:

Column 4, line 55 and 56, "provided another" and insert --above the--.
Column 5, line 25, "blow" should be --blown--.
Column 6, line 30, "comprised" should be --comprises--.
Column 10, line 34, "y" should be --by--.
　　　　　line 48, "heat" should be --hear--.
　　　　　line 68, "1" should be --2--.
Column 12, line 40, "exhales" should be --exhaled--.
Column 14, line 33, after "nated" insert a comma (,).
　　　　　line 62, "along" should be --a long--.
Column 15, line 13, "thereof" should be --thereto--.
　　　　　line 45, "mean" should be --means--.
Column 17, line 48, before "breath" insert --a--.
Column 18, line 8, "along" should be --a long--.

Signed and Sealed this

Third Day of November, 1992

Attest:

DOUGLAS B. COMER

Attesting Officer　　　Acting Commissioner of Patents and Trademarks